United States Patent [19]

Deckner

[11] Patent Number: 4,851,434

[45] Date of Patent: Jul. 25, 1989

[54] NOVEL NON-IRRITATING MOISTURIZER, COMPOSITIONS CONTAINING SAME AND METHOD

[76] Inventor: George E. Deckner, 645 Hort St., Westfield, N.J. 07090

[21] Appl. No.: 499,059

[22] Filed: May 27, 1983

[51] Int. Cl.$^4$ .................. A61K 9/00; A61K 47/00
[52] U.S. Cl. .................. 514/847; 514/625; 564/201; 564/203
[58] Field of Search .................. 564/201, 203; 424/43, 424/358, 365

[56] References Cited

U.S. PATENT DOCUMENTS

| | | | |
|---|---|---|---|
| 2,357,283 | 8/1948 | Peters | 564/203 X |
| 3,028,417 | 4/1962 | Eisenmann | 564/201 X |
| 3,233,988 | 2/1966 | Sexsmith et al. | 564/201 |
| 3,832,367 | 8/1974 | Heiba et al. | |

FOREIGN PATENT DOCUMENTS 2523962  3/1982  France .................. 564/201

Primary Examiner—Robert V. Hines

[57] ABSTRACT

A non-greasy skin moisturizing composition is provided which includes as the major component a compound which has the formula

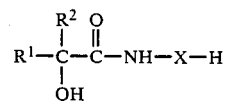

wherein $R^1$ and $R^2$ are the same or different and each may be H or lower alkyl, X is

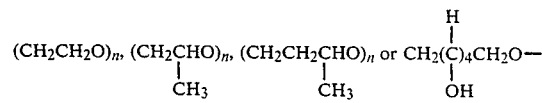

and n is 2 to 20, one or more preservatives and water, and optionally one or more thickeners, one or more skin soothing agents, such as allantoin and/or dl-panthenol, one or more astringents, and/or one or more colorants.

25 Claims, No Drawings

NOVEL NON-IRRITATING MOISTURIZER, COMPOSITIONS CONTAINING SAME AND METHOD

FIELD OF THE INVENTION

The present invention relates to a non-irritating, skin moisturizer which is amide of a di-, tri- or polyglycol or glucamine reaction product with an α-hydroxy-substituted acid, to a moisturizing composition which contains one or more of the above moisturizers and to a method of treating dry skin employing such moisturizer or moisturizing composition containing same.

BACKGROUND OF THE INVENTION

The natural suppleness and moisture in healthy skin is due, in part, to the presence of lactic acid in the skin in the form of sodium lactate. Accordingly, it has been suggested to employ sodium lactate as a humectant or moisturizer in cosmetic and skin treatment compositions for dry skin. Unfortunately, it has been found that when such compositions are applied in the vicinity of the eyes or other areas of sensitive facial skin the sodium lactate in the composition causes irritation and stinging. Thus, a lactate containing moisturizer composition which mimics the natural moisturizing action of sodium lactate in treating dry skin but which is non-irritating and topically efficacious would indeed be a most welcomed addition to the moisturizer field.

DESCRIPTION OF THE INVENTION

In accordance with the present invention, there is provided a moisturizer compound which has the general formula $$R^1 - \underset{\underset{OH}{|}}{\overset{\overset{R^2}{|}}{C}} - \overset{\overset{O}{\|}}{C} - NH - X - H \qquad I$$

wherein $R^1$ and $R^2$ may be the same or different and may be hydrogen or lower alkyl containing from 1 to 5 carbons, such as methyl, ethyl, propyl, isopropyl, n-butyl, sec-butyl or tert-butyl, amyl and the like, with the proviso that at least one of $R^1$ and $R^2$ is lower alkyl, and X is

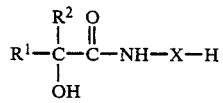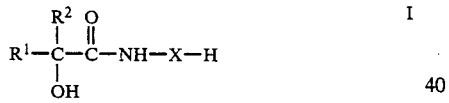

or 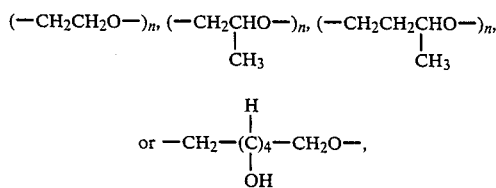

wherein n is an integer from 2 to 20. In the preferred moisturizer compounds of the invention $R^1$ is lower alkyl containing from 1 to 5 carbons, for example, methyl, $R^2$ is H, X is $(-CH_2CH_2O-)_n$ wherein n is 2 to 4, or X is

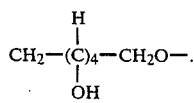

Further, in accordance with the present invention, an improved non-irritating moisturizing composition is provided which is especially suited for treating dry skin and includes as the major moisturizing component the di-, tri-, or polyglycol amide or glucamine reaction product with an α-hydroxy-substituted fatty acid, as described above, having formula I except that either or both of $R^1$ and $R^2$ may be hydrogen or lower alkyl, one or more preservatives, and water as the carrier. The moisturizer composition will also preferably include one or more thickeners, one or more skin conditioning agents, one or more skin feel enhancers, one or more astringents, and/or colorants and/or fragrances. The above moisturizing composition of the invention may be in the form of a clear gel, solution, lotion or cream.

The major moisturizing component for use in the compositions of the invention will thus have the following formulae

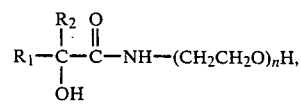 II

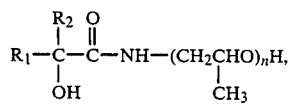 III

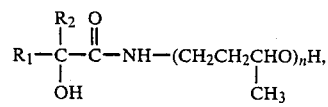 IV or

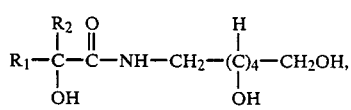 V

Preferred major moisturizing components are those of formula II wherein n is 2 to 4, R is H or lower alkyl and $R^2$ is H or lower alkyl. More preferred are compounds of formula II wherein $R^1$ $CH_3$, $R^2$ is H and n is 2, and compounds of formula V wherein $R^1$ is $CH_3$ and $R^2$ is H. The more preferred major moisturizing component may have the formula

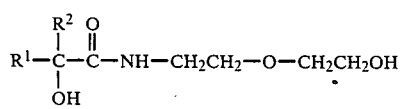 VI or

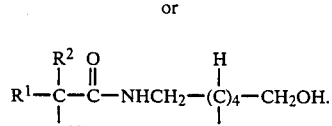 VII

In each case, it is most preferred that $R^1$ is methyl and $R^2$ is hydrogen.

The above major moisturizing component may be produced by known methods. For example, they can be obtained by reacting equimolar quantities of an α-hydroxy acid ester of the structure

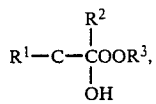

wherein $R^1$ and $R^2$ are as defined above and $R^3$ is lower alkyl (such as glycolic acid ester, lactic acid ester, α-hydroxybutyric acid ester and the like) with the appropriate amine of the structure $NH_2-(X)_n-OH$ following the procedure as described in U.S. Pat. No. 2,347,494. Alternatively, procedures as described in U.S. Pat. No. 4,143,159 may be employed.

The major moisturizing component will be present in the moisturizing composition in an amount within the range of from about 1 to about 20% and preferably from about 1 to about 10% by weight.

The component for providing enhanced skin feel will comprise a polyol which will be present in an amount within the range of from about 0.5 to about 20% and preferably from about 3 to about 10% by weight. Examples of such polyols (which also serve as humectants) suitable for use herein include, but are not limited to, polyethylene glycol (for example, PEG 8), sorbitol, glycerol, propylene glycol, 1,3-butylene glycol, hexylene glycol or polyoxyethylene 26 glycerine with glycerol and polyethylene glycol 8 (that is, made from 8 moles of ethylene oxide) being preferred.

The moisturizing composition of the invention will also include from about 0.05 to about 1.5% and preferably from about 0.1 to about 1% by weight of a preservative, such as imidazolidinyl urea (for example, Germall 115), methyl paraben, dimethyldimethoyl hydantoin, Dowicil 200 (Quaternium 15), that is N-(3-chloroallyl)-hexaminium chloride, benzyl alcohol and/or phenoxyethanol, with imidazolidinyl urea and methyl paraben being preferred.

Water will be employed in the moisturizing composition of the invention as the primary solvent and carrier and will be present in an amount within the range of form about 50 to about 90% and preferably from about 60 to about 80% by weight.

The moisturizing composition of the invention will optionally include a thickener in an amount within the range of from about 0.05 to about 1% and preferably from about 0.05 to about 0.3% by weight. A preferred thickener suitable for use herein is Carbonol 940 or Carbomer 940 which is hydrophilic acrylic polymer cross-linked with a polyfunctional agent and employed with an organic or inorganic base, preferably triethanolamine. Other examples of thickeners which may be employed herein include, but are not limited to, hydroxyethyl cellulose, hydroxypropyl cellulose or xanthan gum.

Skin conditioning agents which may optionally be present in the moisturizing composition of the invention include allantoin, d- or dl-panthenol, hydrolyzed animal protein and the like. Such conditioning agents may be present in an amount within the range of from about 0.01 to about 5% and preferably from about 0.05 to about 2% by weight.

The astringents which may optionally be included will be present in an amount within the range of from about 1 to about 20% and preferably from about 3 to about 10% by weight of the moisturizing composition of the invention. Examples of such astringents suitable for use herein include ethanol and isopropyl alcohol.

The moisturizing composition of the invention may also be employed in formulating clear skin toners, after shave lotions, colognes, after-sun products, makeup or cosmetics and the like. Accordingly, such skin preparations may include, in addition to the ingredients set out above, certified water-soluble colorants as deemed necessary, fragrances in amounts within the range of from about 0 to about 35% and preferably from about 0.1 to about 20% by weight depending upon the ultimate use of the skin preparation, solubilizing agents, such as polyoxyethylene (13) octylphenyl ether, polyoxyethylene 20 sorbitan laurate, polyoxyethylene 20 oleyl ether, and the like.

Preferred formulations within the scope of the present invention contain from about 1 to about 5% by weight major moisturizer component as defined above [preferably N-[2-(2-hydoxyethoxy)ethyl]lactamide

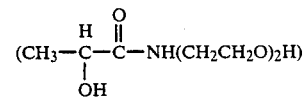

or or N-lactoylglycamine

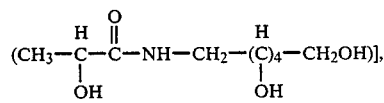

from about 2 to about 10% by weight glycerin and/or polyethylene glycol, from about 0.1 to about 1% by weight imidazolidinyl urea and/or other preservatives, from about 60 to about 80% by weight water, optionally from about 0.05 to about 0.5% carboxymethyl cellulose, optionally from about 0.05 to about 2% by weight allantoin and/or panthenol, optionally from about 3 to about 20% by weight ethanol and/or isopropyl alcohol.

The skin preparations of the invention containing the moisturizing composition as set out above can be prepared as follows. Where the moisturizer composition is to be in the form of a clear lotion or gel, then all of the ingredients may be simply mixed together, preferably without heat, if possible, and then bottled.

The following Examples represent preferred embodiments of the invention.

EXAMPLE 1

N-[2-(2-Hydroxyethoxy)ethyl]lactamide (Reaction product of 2-(2-aminoethoxy)ethanol and lactic acid)

Equimolar quantities of lactic acid and 2-(2-aminoethoxy)ethanol were mixed together. This mixture was then heated to 120° for 2 hours and the resulting water of reaction was continuously removed. The final product was a viscous, amber colored liquid.

EXAMPLE 2

A moisturizing composition for use in treating dry skin and having the following composition was prepared as described below.

| Ingredient | Parts by Weight |
| --- | --- |
| Mix A | |
| Deionized water (diluent) | 70 |
| Magnesium aluminum silicate (thickener, stabilizer) | 0.4 |

-continued

| Ingredient | Parts by Weight |
| --- | --- |
| Carboxy methyl cellulose (thickener, stabilizer) | 0.2 |
| dl-Panthenol (skin protecting agent) | 0.2 |
| Glycerin (humectant) | 4 |
| Carbowax 400 (PEG 8-humectant) | 1 |
| Methyl paraben (preservative) | 0.2 |
| Xanthan gum (thickener, stabilizer) | 0.2 |
| Mix B | |
| Octyl dimethyl para-aminobenzoic acid (sunscreen) | 2 |
| Benzophenone-3 (sunscreen) | 0.5 |
| Propylene glycol dicaprylate/dicaprate (emollient) | 4 |
| Mineral oil (emollient) | 4 |
| Propyl paraben (preservative) | 0.1 |
| Butyl paraben (preservative) | 0.1 |
| Stearic acid (thickener) | 1.5 |
| Glyceryl monostearate and PEG 100 stearate (emulsifier, thickener) | 2 |
| Stearoxydimethicone (thickener, improve barrier properties) | 1.5 |
| Dimethicone (emollient) | 1 |
| Steareth 20 (emulsifier) | 1.3 |
| Mix C | |
| Reaction product of 2-(2-amino-ethoxyethanol and lactic acid (prepared as described in Example 1) | 2 |
| Deionized water | 2 |
| Mix D | |
| Sodium lauroyl sarcosinate (feel enhancer) | 0.1 |
| Deionized water | 2 |
| Mix E | |
| Deionized water | 1 |
| N—(3-Chloroallyl)hexaminium chloride | 0.15 |

Each of Mixes A and B were heated to 75° C. and Mix B was added to Mix A with propeller type mixing while maintaining the 75° C. temperature for 1 hour. The resulting mixture was cooled to 65° C. and Mix C was added. The mixture was then cooled to 50° C. and Mix D and Mix E were added. Cooling was continued to 30° C. to form the protective daytime lotion/moisturizer of the invention which was found to have improved feel and barrier properties, was naturally compatible with the skin and had improved skin penetrability.

EXAMPLE 3

N-Lactoylglucamine (Reaction product of glucamine and lactic acid)

Equimolar quantities of lactic acid and glucamine were mixed together. This mixture was then heated at 120° C. for 2 hours and the resulting water of reaction was continuously removed. The final product was a viscous, amber colored liquid.

EXAMPLE 4

Following the procedure of Example 2, a moisturizer formulation was prepared which was similar to that prepared in Example 2 except that the Example 4 glucamide was used in place of the Example 1 diglycolamide. The resulting formulation was found to have excellent moisturizing properties and improve skin penetrability.

What is claimed is:

1. A compound having the structure

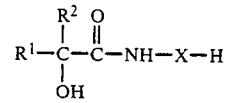

wherein $R^1$ and $R^2$ are the same or different and are selected from the group consisting of hydrogen and lower alkyl containing 1 to 5 carbons, provided that at least one of $R^1$ and $R^2$ is lower alkyl, and X is $$(-CH_2CH_2O-)_n, (-CH_2CHO-)_n, (-CH_2CH_2CHO-)_n \text{ or}$$
$$\phantom{(-CH_2CH_2O-)_n, (-CH_2CH}CH_3 \phantom{H_2CHO-)_n, (-}CH_3$$

$$(-CH_2CH_2O-)_n$$

$$-CH_2(-\underset{\underset{OH}{|}}{\overset{\overset{H}{|}}{C}}-)_4CH_2O-$$

wherein n is an integer from 2 to 20.

2. The compound as defined in claim 1 wherein X is wherein n is 2 to 5.

3. The compound as defined in claim 2 wherein X is $(-CH_2CH_2O-)_2$.

4. The compound as defined in claim 1 wherein X is $$-CH_2(-\underset{\underset{OH}{|}}{\overset{\overset{H}{|}}{C}}-)_4CH_2O-.$$

5. The compound as defined in claim 1 wherein $R^1$ is lower alkyl and $R^2$ is H.

6. The compound as defined in claim 1 having the formula

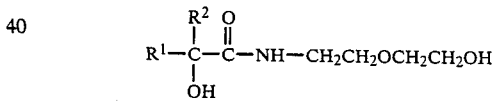

wherein $R^1$ is $CH_3$ and $R^2$ is H.

7. The compound as defined in claim 1 having the formula

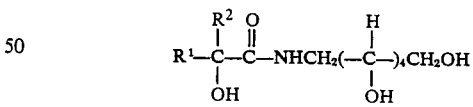

wherein $R^1$ is $CH_3$ and $R^2$ is H.

8. A non-irritating moisturizer composition which comprises a major moisturizing component having the formula

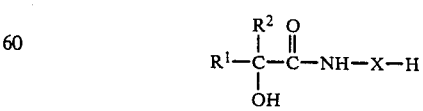

wherein X is $$(-CH_2CH_2O-)_n, (-CH_2CHO-)_n, (-CH_2CH_2CHO-)_n \text{ or}$$
$$\phantom{(-CH_2CH_2O-)_n, (-CH_2CH}CH_3 \phantom{H_2CHO-)_n, (-}CH_3$$

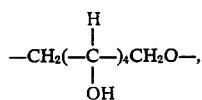

n is 2 to 20, $R^1$ and $R^2$ are the same or different and are selected from the group consisting of H or lower alkyl.

9. The composition as defined in claim 8 wherein the major moisturizing component has the formula

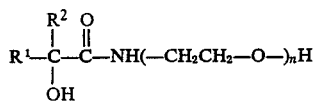

wherein n is 2 to 5.

10. The composition as defined in claim 9 wherein n is 2.

11. The composition as defined in claim 10 wherein $R^1$ is $CH_3$ and $R^2$ is H.

12. The composition as defined in claim 8 wherein the major moisturizing component has the formula

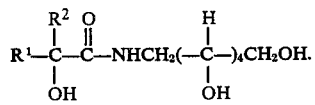

13. The composition as defined in claim 12 wherein $R^1$ is $CH_3$ and $R^2$ is H.

14. The composition as defined in claim 8 further including one or more preservatives and water.

15. The composition as defined in claim 14 further including one or more skin smoothing or conditioning agents in an amount within the range of from about 0.01 to about 5% by weight or one or more thickeners in an amount within the range of from about 0.05 to about 1% by weight.

16. The composition as defined in claim 14 further including one or more alcohol astringents in an amount within the range of from about 1 to about 20% by weight.

17. The composition as defined in claim 14 further including one or more thickeners, one or more skin conditioning agents, one or more astringents and optionally one or more fragrances.

18. The composition as defined in claim 14 wherein the major moisturizing component is present in an amount within the range of from about 1 to about 20% by weight.

19. The composition as defined in claim 14 wherein the preservative is present in an amount within the range of from about 0.05 to about 1.5%.

20. The composition as defined in claim 19 wherein the preservative is imidazolidinyl urea, propyl paraben, butyl paraben, methyl paraben, dimethyl dimethoyl hydantoin, N-(3-chloroallyl)-hexaminium chloride, benzyl alcohol, phenoxyethanol or mixtures of two or more thereof.

21. The composition as defined in claim 14 wherein the water is present in an amount within the range of from about 50 to about 90% by weight.

22. The composition as defined in claim 15 wherein the skin soothing agent is allantoin, panthenol or mixtures thereof.

23. The composition as defined in claim 8 in the form of a skin toner, emulsion, cologne, make-up, skin moisturizer, moisturizing aerosol spray, a moisturizing after-sun product, powder, cream or lotion.

24. A method for treating dry skin which comprises applying to the skin a moisturizer having the formula as defined in claim 1.

25. A method for treating dry skin which comprises applying to the skin a moisturizing composition as defined in claim 8.

* * * * *